(12) United States Patent
Kuang et al.

(10) Patent No.: US 10,525,016 B2
(45) Date of Patent: Jan. 7, 2020

(54) NUTRITIONAL COMPOSITIONS CONTAINING AN ELEVATED LEVEL OF INOSITOL AND USES THEREOF

(71) Applicant: Mead Johnson Nutrition Company, Glenview, IL (US)

(72) Inventors: Chenzhong Kuang, Newburgh, IN (US); Yan Xiao, Newburgh, IN (US); Colin Rudolph, San Francisco, CA (US); Dirk Hondmann, Winnetka, IL (US)

( * ) Notice: Subject to any disclaimer, the term of this patent is extended or adjusted under 35 U.S.C. 154(b) by 0 days.

(21) Appl. No.: 14/729,132

(22) Filed: Jun. 3, 2015

(65) Prior Publication Data
US 2016/0354323 A1 Dec. 8, 2016

(51) Int. Cl.
| A61K 31/047 | (2006.01) |
| A61K 31/715 | (2006.01) |
| A61K 47/12 | (2006.01) |
| A61K 47/26 | (2006.01) |
| A61K 47/42 | (2017.01) |
| A23L 1/29 | (2006.01) |

(52) U.S. Cl.
CPC .......... *A61K 31/047* (2013.01); *A61K 31/715* (2013.01); *A61K 47/12* (2013.01); *A61K 47/26* (2013.01); *A61K 47/42* (2013.01); *A23V 2002/00* (2013.01)

(58) Field of Classification Search
CPC .... A61K 31/047; A61K 31/715; A61K 47/26; A61K 47/12; A61K 47/42; A23L 1/296; A23V 2002/00
USPC .................................................. 514/54, 738
See application file for complete search history.

(56) References Cited

U.S. PATENT DOCUMENTS

| 4,791,193 A | 12/1988 | Okonogi et al. |
| 4,921,877 A | 5/1990 | Cachmere et al. |
| 5,032,399 A | 7/1991 | Gorbach et al. |
| 5,340,603 A | 8/1994 | Neylan et al. |
| 5,374,567 A | 12/1994 | Cartagena |
| 5,397,591 A | 3/1995 | Kyle |
| 5,550,156 A | 8/1996 | Kyle |
| 5,763,392 A | 6/1998 | Hansen et al. |
| 5,849,885 A | 12/1998 | Nuyens |
| 5,861,491 A | 1/1999 | Nuijens |
| 5,919,913 A | 7/1999 | Nuyens |
| 6,039,985 A | 3/2000 | Kamarei |
| 6,194,009 B1 | 2/2001 | Kamarel |
| 6,620,326 B1 | 9/2003 | Lihme |
| 6,977,046 B2 | 12/2005 | Hubbuch |
| 7,368,141 B2 | 5/2008 | Lihme |
| 7,687,652 B2 | 3/2010 | Rochlin et al. |
| 7,812,138 B2 | 10/2010 | Lihme |
| 7,867,541 B2 | 1/2011 | McMahon |
| 7,951,410 B2 | 5/2011 | McMahon |
| 8,287,932 B2 | 10/2012 | Rosales et al. |
| 9,226,914 B2* | 1/2016 | Kuang ............... A23L 33/40 |
| 9,241,923 B2* | 1/2016 | Kuang ............... A23L 33/10 |
| 2003/0099722 A1 | 2/2003 | Lanham |
| 2003/0134851 A1 | 7/2003 | Baxter et al. |
| 2008/0003329 A1* | 1/2008 | Rueda ............... A23L 33/40 426/72 |
| 2008/0003330 A1 | 1/2008 | Rueda et al. |
| 2008/0057178 A1 | 3/2008 | Rueda et al. |
| 2008/0064635 A1 | 3/2008 | Rueda et al. |
| 2012/0171328 A1* | 7/2012 | Banavara ............ A23C 11/04 426/61 |
| 2012/0321600 A1 | 12/2012 | Benyacoub et al. |
| 2013/0291737 A1 | 11/2013 | Sims |
| 2014/0105875 A1* | 4/2014 | Bolster .............. A23C 9/1512 424/93.45 |
| 2014/0179775 A1 | 6/2014 | Kuang |
| 2014/0200176 A1 | 7/2014 | Berg |
| 2015/0023922 A1 | 1/2015 | Kuang |
| 2015/0023923 A1 | 1/2015 | Kuang et al. |
| 2015/0037455 A1 | 2/2015 | Chichlowski et al. |
| 2015/0119322 A1 | 4/2015 | Chichlowski et al. |

FOREIGN PATENT DOCUMENTS

| EP | 2046149 | 11/2010 |
| WO | 1992000799 | 1/1992 |
| WO | 1992018237 | 10/1992 |
| WO | 1997017132 | 5/1997 |
| WO | 2000065934 | 11/2000 |
| WO | 2002018237 | 3/2002 |
| WO | 2004032653 | 4/2004 |
| WO | 2006076425 | 7/2006 |
| WO | 2008005032 | 1/2008 |

(Continued)

OTHER PUBLICATIONS

Murray, M.T. Encyclopedia of Nutritional Supplements, Prima Health, 1996, pp. 142-144.*
Susuki, Keiichiro, Nature Education, 2010, 3(9), pp. 1-3.*
Bemiller, J., "An Introduction to Pectins: Structure and Properties," Chemistry and Function of Pectins; Chapter 1; 1986.
Brown, L. D., A. Cheung, et al. (2009). "Inositol and mannose utilization rates in term and late-preterm infants exceed nutritional intakes." J Nutr 139(9): 1648-1652.
Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, Aug. 2005.
Harzer, G. et al., "Changing patterns of human milk lipids in the course of the lactation and during the day," Am. J. Clin. Nutr., vol. 37, pp. 612-621 (1983).

(Continued)

*Primary Examiner* — Ganapathy Krishnan
(74) *Attorney, Agent, or Firm* — Troutman Sanders LLP; Ryan Schneider; Chris Davis

(57) ABSTRACT

A method for enhancing neurological health and development in a subject involving administering to the subject a nutritional composition including no greater than about 7 g/100 kcal of a fat or lipid source; no greater than about 7 g/100 kcal of a protein or protein equivalent source; at least about 5 g/100 kcal of a carbohydrate; and at least about 9 mg/100 kcal of inositol, wherein the ratio of exogenous inositol to inherent inositol is at least 50:50.

8 Claims, 7 Drawing Sheets

(56) References Cited

FOREIGN PATENT DOCUMENTS

| WO | 2008005033 | 1/2008 |
|---|---|---|
| WO | 2008005862 | 1/2008 |
| WO | 2008005869 | 1/2008 |
| WO | 2011069987 | 6/2011 |
| WO | 2015009406 | 1/2015 |

OTHER PUBLICATIONS

Silver, S. M., B. M. Schroeder, et al. (2002). "Brain uptake of myoinositol after exogenous administration." J Am Soc Nephrol 13(5): 1255-1260.

Spector, R. (1988). "Myo-inositol transport through the blood-brain barrier." Neurochem Res 13(8): 785-787.

Yadomae, T., "Structure and biological activities of fungal beta-1,3-glucans." Yakugaku Zasshi. 2000;120:413-431.

Anonymous: "Standard for Infant Formula and Formulas for Special Medical Purposes Intended for Infants," Jan. 1, 1981, http://www.fao.org/input/dowload/standards/288/CXS_072e_2015.pdf [retrieved on Jun. 23, 2016].

Chen, L., et al., "Determination of Myo-Inositol (Free and Bound as Phosphatidylinositol) in Infant Formula and Adult Nutritionals," Jan. 1, 2014, http://www.dionex.com/en-us/webdocs/115221-AN1083-IC-Myo-Inositol-Inf.Formula-AdultNutrit-AN70908-E.pdf [retrieved on Jun. 24, 2016].

Hallman, M., et al., "Inositol Supplementation in Premature Infants with Respiratory Distress Syndrome," N Engl J Med 1992;326:1233-9.

Burry, R., et al., "Formation of Apparent Presynaptic Elements in Response to Poly-Basic Compounds," Brain Research, 184 (1980) 85-98.

Burry, R., et al., "Highly Basic 30- and 32-Kilodalton Proteins Associated with Synapse Formation on Polylysine-Coated Beads in Enriched Neuronal Cell Cultures," J. Neurochem. 52, 55 1-560 (1989).

Cavalli, C., et al., "Free Sugar and Sugar Alcohol Concentrations in Human Breast Milk," Journal of Pediatric Gastroenterology and Nutrition 42:215-221, 2006.

Dai, Z., et al., "Dynamics of Synaptic Vesicles in Cultured Spinal Cord Neurons in Relationship to Synaptogenesis," Molecular and Cellular Neuroscience 7, 443-452 (1996).

Huttenlocher, P., et al., "Regional Differences in Synaptogenesis in Human Cerebral Cortex," The Journal of Comparative Neurology 387:167-178 (1997).

Lucido, A., et al., "Rapid Assembly of Functional Presynaptic Boutons Triggered by Adhesive Contacts," The Journal of Neuroscience, Oct. 7, 2009 29(40):12449-12466.

Marszalek, J., et al., "Long-chain Acyl-CoA Synthetase 6 Preferentially Promotes DHA Metabolism*," vol. 280, No. 11, Issue of Mar. 18, pp. 10817-10826, 2005.

Mauch, D., et al., "CNS Synaptogenesis Promoted by Glia-Derived Cholesterol," Science Nov. 9, 2001 vol. 294, pp. 1354-1357.

Missler, M. et al., "Synaptic Cell Adhesion," Cold Spring Harb Perspect Biol 2012;4:a005694, Jan. 25, 2012.

Rakic, P., et al., "Concurrent Overproduction of Synapses in Diverse Regions of the Primate Cerebral Cortex," Science Dec. 6, 1985, vol. 232, pp. 232-235.

Shen, K, et al., "Genetics and Cell Biology of Building Specific Synaptic Connectivity," Annu Rev Neurosci. 2010; 33: 473-507. doi:10.1146/annurev.neuro.051508.135302.

Slutsky, I., et al., "Enhancement of Learning and Memory by Elevating Brain Magnesium," Neuron 65, 165-177, Jan. 28, 2010.

Washbourne, P., et al., "Cell Adhesion Molecules in Synapse Formation," The Journal of Neuroscience, Oct. 20, 2004 24(42):9244-9249.

\* cited by examiner

Myelin extent

NUTRITIONAL COMPOSITIONS CONTAINING AN ELEVATED LEVEL OF INOSITOL AND USES THEREOF

TECHNICAL FIELD

The present disclosure relates to nutritional compositions that include inositol at levels found to provide neurological benefits. More particularly, the disclosed nutritional compositions include a fat, a carbohydrate, a protein or protein equivalent source, and inositol, for improving neurological health and/or preventing or protecting against the development of neurodegenerative diseases. The nutritional compositions described herein are suitable for administration to adult and pediatric subjects.

BACKGROUND

The nervous system is responsible for accumulating and analyzing sensory input and coordinating the generation of the appropriate functional response. The successful execution and integration of these activities is dependent on the transmission of neuronal action potentials, electrical signals required to generate functional outputs. While it is the neuronal cell that is responsible for the actual conduction of the signaling current, the rate at which the signal travels is greatly enhanced by the insulating properties of its glial-derived myelin sheath. In the central nervous system (CNS), glial cells known as oligodendrocytes are responsible for the formation of myelin. These terminally differentiated cells arise from progenitors termed oligodendrocyte precursor cells (OPCs). During development, OPCs are exposed to proliferative signals as they migrate along axons throughout the CNS. These developmental cues help ensure that the extent of OPC proliferation is sufficient to generate the appropriate number of oligodendrocytes to myelinate all relevant axonal segments. Once the required number of precursor cells has been generated, the differentiation process initiates followed by myelination.

Therefore, the impacts on the myelination process by brain nutrients are integrated by three basic aspects: (1) the survival and proliferation of oligodendritic projector cells (OPCs); (2) the differentiation of OPCs into oligodendric cells (Oligo); and myelination deposition.

Myelination and synapse development are very important for neurological health. This is true in infants and children, for brain development and to provide improvement in specific brain function such as cognition, memory function, learning capacity, social interaction skills, reduced anxiety, visual acuity, motor skills and/or language skills. Likewise, improved myelination and synapse development can be beneficial in adults, especially adults with neurodegenerative diseases like Alzheimer's disease.

Myelination can be described as the process by which a fatty layer, called myelin, accumulates around nerve cells (neurons), and begins in infancy and continues through adulthood. Myelin particularly forms around the long shaft, or axon, of neurons. Myelination enables nerve cells to transmit information faster and allows for more complex brain processes. Thus, the process is vitally important to healthy central nervous system functioning.

In the nervous system, a synapse is a structure that permits a neuron to pass an electrical or chemical signal to another cell (neural or otherwise). Thus, synapses are essential to neuronal function: neurons are cells that are specialized to pass signals to individual target cells, and synapses are the means by which they do so. At a synapse, the plasma membrane of the signal-passing neuron (the presynaptic neuron) comes into close apposition with the membrane of the target (postsynaptic) cell. Both the presynaptic and postsynaptic sites contain extensive arrays of molecular machinery that link the two membranes together and carry out the signaling process. Synapse development, or synaptogenesis, is the formation of synapses between neurons in the nervous system. Although it occurs throughout a healthy person's lifespan, an explosion of synapse formation occurs during early brain development, known as exuberant synaptogenesis.

Myelination begins in the brain stem and cerebellum before birth, but is not completed in the frontal cortex until late in adolescence. Breast feeding contributes to more rapid myelination in the brain. Identification of nutrients that promote survival and proliferation of oligodendrocytes represents a major unmet need. Beyond normal development, white matter injury is one of the leading causes of neurological disease in infants, especially in infants born premature. In these cases, oligodendrocyte cell death and a lack of developmental myelination represent leading factors, resulting in aberrant neural circuit formation and nervous system refinement.

Thus, it would be useful to provide nutritional compositions that are able to improve myelination and synapse development in a subject. In particular, it may be useful to provide improved neurological health and function, including cognition, language development and motor skills in early life in order to reduce or prevent adult neurological diseases. It would also be useful to combat neurodegenerative disease through improved myelination and synapse development in adults.

Accordingly, the present disclosure provides a nutritional composition including inositol as described herein. In some embodiments, the nutritional composition also includes a fat or lipid, carbohydrate and protein or protein equivalent source.

BRIEF SUMMARY

Briefly, the present disclosure is directed, in an embodiment, to a nutritional composition comprising exogenous inositol, and to a method for providing improved neurological health and function, including cognition, language development and motor skills in early life in order to reduce or prevent adult neurological diseases, in a pediatric subject, the method comprising administering to the pediatric subject a nutritional composition comprising inositol, a fat or lipid, a protein or protein equivalent source and a carbohydrate. In some embodiments, the nutritional composition can also include one or more long chain polyunsaturated fatty acids (LCPUFAs) selected from the group consisting of docosahexaenoic acid (DHA) and arachidonic acid (ARA), phosphatidylethanolamines (PE), sphingomyelin (SPM), alpha-lipoic acid (ALA), epigallocatechin gallate (EGCG), sulforaphane, or combinations thereof, which may synergistically combine with inositol to further improve neurological health and development.

In certain embodiments, the nutritional composition further comprises an enriched lipid fraction derived from milk. In some embodiments the nutritional composition may include an enriched lipid fraction derived from milk that includes milk fat globules. The addition of the milk fat globules provides an enriched fat and lipid source to the infant that may be more fully digested by a pediatric subject.

In embodiments, the enriched lipid fraction and/or the milk fat globules may include saturated fatty acids, trans-fatty acids, monounsaturated fatty acids, polyunsaturated fatty acids, cholesterol, odd-branched chain fatty acids "OBCFAs", branched chain fatty acids "BCFAs", conjugated linoleic acid "CLA", phospholipids, or milk fat globule membrane protein, and mixtures thereof.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Figure 1:
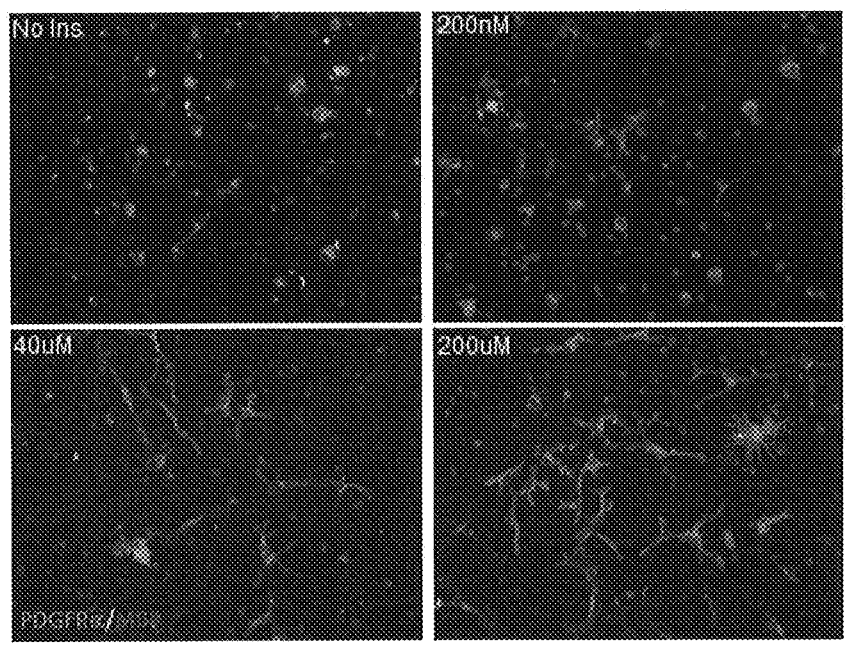
FIG. 1 illustrates a dose-response for inositol on purified oligodendrogial cultures, resulting from the testing of Example 1.

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to nutritional compositions that are suitable for administration to a pediatric subject. Additionally, the disclosure relates to methods for improving neurological health and development in children and adults via administration of the nutritional composition(s) disclosed herein.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human no greater than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the 37th week of gestation. "Late preterm" means an infant from between the 34th week and the 36th week of gestation. "Full term" means an infant born after the end of the 37th week of gestation. "Low birth weight infant" means an infant born weighing less than 2500 grams (approximately 5 lbs, 8 ounces). "Very low birth weight infant" means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

The term "degree of hydrolysis" refers to the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

The term "partially hydrolyzed" means having a degree of hydrolysis which is greater than 0% but less than about 50%.

The term "extensively hydrolyzed" means having a degree of hydrolysis which is greater than or equal to about 50%.

The term "protein-free" means containing no measurable amount of protein, as measured by standard protein detection methods such as sodium dodecyl (lauryl) sulfate-polyacrylamide gel electrophoresis (SDS-PAGE) or size exclusion chromatography. In some embodiments, the nutritional composition is substantially free of protein, wherein "substantially free" is defined hereinbelow.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Milk" means a component that has been drawn or extracted from the mammary gland of a mammal. In some embodiments, the nutritional composition comprises components of milk that are derived from domesticated ungulates, ruminants or other mammals or any combination thereof.

"Fractionation procedure" includes any process in which a certain quantity of a mixture is divided up into a number of smaller quantities known as fractions. The fractions may be different in composition from both the mixture and other fractions. Examples of fractionation procedures include but are not limited to, melt fractionation, solvent fractionation, supercritical fluid fractionation and/or combinations thereof.

"Fat globule" refers to a small mass of fat surrounded by phospholipids and other membrane and/or serum proteins, where the fat itself can be a combination of any vegetable or animal fat.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts a beneficial effect on the health of the host.

The term "inactivated probiotic" means a probiotic wherein the metabolic activity or reproductive ability of the referenced probiotic has been reduced or destroyed. The "inactivated probiotic" does, however, still retain, at the cellular level, its cell structure or other structure associated with the cell, for example exopolysaccharide and at least a portion its biological glycol-protein and DNA/RNA structure. As used herein, the term "inactivated" is synonymous with "non-viable".

"Prebiotic" means a non-digestible food ingredient that beneficially affects the host by selectively stimulating the growth and/or activity of one or a limited number of bacteria in the digestive tract that can improve the health of the host.

"Inherent inositol", "endogenous inositol" or "inositol from endogenous sources" each refer to inositol present in the composition that is not added as such, but is present in other components or ingredients of the composition; the inositol is naturally present in such other components. Contrariwise, "exogenous" inositol is inositol which is intentionally included in the nutritional composition of the present disclosure itself, rather than as an element of another component.

"Branched Chain Fatty Acid" ("BCFA") means a fatty acid containing a carbon constituent branched off the carbon chain. Typically the branch is an alkyl branch, especially a methyl group, but ethyl and propyl branches are also known. The addition of the methyl branch lowers the melting point compared with the equivalent straight chain fatty acid. This includes branched chain fatty acids with an even number of carbon atoms in the carbon chain. Examples of these can be isomers of tetradecanoic acid, hexadecanoic acid.

"Odd- and Branched-Chain Fatty Acid" ("OBCFA") is a subset of BCFA that has an odd number of carbon atoms and have one or more alkyl branches on the carbon chain. The main odd- and branched-chain fatty acids found in bovine milk include, but are not limited to, the isomers of tetradecanoic acid, pentadecanoic acid, hexadecanoic acid, and heptadecanoic acid. For the purposes of this disclosure, the term "BCFA" includes both branched-chain fatty acids and odd-and-branched chain fatty acids.

"Trans-fatty acid" means an unsaturated fat with a trans-isomer. Trans-fats may be monounsaturated or polyunsaturated. Trans refers to the arrangement of the two hydrogen atoms bonded to the carbon atoms involved in a double bond. In the trans arrangement, the hydrogens are on opposite sides of the bond. Thus a trans-fatty acid is a lipid molecule that contains one or more double bonds in trans geometric configuration.

"Phospholipids" means an organic molecule that contains a diglyceride, a phosphate group and a simple organic molecule. Examples of phospholipids include but are not limited to, phosphatidic acid, phosphatidylethanolamine, phosphatidylcholine, phosphatidylserine, phsphatidylinositol, phosphatidylinositol phosphate, phosphatidylinositol biphosphate and phosphatidylinositol triphosphate, ceramide phosphorylcholine, ceramide phosphorylethanolamine and ceramide phosphorylglycerol. This definition further includes sphigolipids, glycolipids, and gangliosides.

"Phytonutrient" means a chemical compound that occurs naturally in plants. Phytonutrients may be included in any plant-derived substance or extract. The term "phytonutrient(s)" encompasses several broad categories of compounds produced by plants, such as, for example, polyphenolic compounds, anthocyanins, proanthocyanidins, and flavan-3-ols (i.e. catechins, epicatechins), and may be derived from, for example, fruit, seed or tea extracts. Further, the term phytonutrient includes all carotenoids, phytosterols, thiols, and other plant-derived compounds. Moreover, as a skilled artisan will understand, plant extracts may include phytonutrients, such as polyphenols, in addition to protein, fiber or other plant-derived components. Thus, for example, apple or grape seed extract(s) may include beneficial phytonutrient components, such as polyphenols, in addition to other plant-derived substances.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

"Pectin" means any naturally-occurring oligosaccharide or polysaccharide that comprises galacturonic acid that may be found in the cell wall of a plant. Different varieties and grades of pectin having varied physical and chemical properties are known in the art. Indeed, the structure of pectin can vary significantly between plants, between tissues, and even within a single cell wall. Generally, pectin is made up of negatively charged acidic sugars (galacturonic acid), and some of the acidic groups are in the form of a methyl ester group. The degree of esterification of pectin is a measure of the percentage of the carboxyl groups attached to the galactopyranosyluronic acid units that are esterified with methanol.

Pectin having a degree of esterification of less than 50% (i.e., less than 50% of the carboxyl groups are methylated to form methyl ester groups) are classified as low-ester, low methoxyl, or low methylated ("LM") pectins, while those having a degree of esterification of 50% or greater (i.e., more than 50% of the carboxyl groups are methylated) are classified as high-ester, high methoxyl or high methylated ("HM") pectins. Very low ("VL") pectins, a subset of low methylated pectins, have a degree of esterification that is less than approximately 15%.

As used herein, "lactoferrin from a non-human source" means lactoferrin which is produced by or obtained from a source other than human breast milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism.

As used herein, "non-human lactoferrin" means lactoferrin that has an amino acid sequence that is different than the amino acid sequence of human lactoferrin.

"Pathogen" means an organism that causes a disease state or pathological syndrome. Examples of pathogens may include bacteria, viruses, parasites, fungi, microbes or combination(s) thereof.

"Modulate" or "modulating" means exerting a modifying, controlling and/or regulating influence. In some embodiments, the term "modulating" means exhibiting an increasing or stimulatory effect on the level/amount of a particular component. In other embodiments, "modulating" means exhibiting a decreasing or inhibitory effect on the level/amount of a particular component.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to nutritional compositions comprising inositol, to uses thereof, and to methods comprising administration of those nutritional compositions to a pediatric or adult subject. The nutritional compositions of the present disclosure support and improve neurological health and development.

Inositol is transported across the blood-brain barrier by simple diffusion and a stereospecific saturation transport system. Moreover, the brain can take up inositol after exogenous administration. It has thus been found that oral administration of inositol can engender enhance neurological conditions for brain benefits.

It has been found that nutritional supplementation of inositol represents a feasible and effective approach to promote oligodendrocyte survival and proliferation in a dose dependent manner, resulting in a consistent increase in the number of oligodendrocyte precursor cells. Nutritional supplementation with inositol provides benefits for enhanced developmental myelination by which it translates into a fundamental benefit for brain development. Given the importance of functional myelination, nutritional supplementation of inositol is beneficial to pediatric and adult subjects by enhancing brain development and health. Because the nature and characteristics of inositol allow it to cross the blood brain barrier, inositol can be considered a novel brain nutrient, synergizing with other nutrients to provide comprehensive brain development benefits. Moreover, the positive effects on enhanced developmental myelination from inositol can be beneficial for preterm infants as well as those diagnosed with white matter diseases (such as cerebral palsy and periventricular leukomalacia). Inositol can also be beneficial in other situations where myelination can be an issue, such as with patients having multiple sclerosis and in post radiation supplementation for promotion of recovery of OPCs. Moreover, the sweet taste of inositol provides further advantages in terms of palatability to consumers, especially infants and children.

In certain embodiments, inositol is present in the nutritional compositions of the present disclosure at a level of at least about 9 mg/100 kcal; in other embodiments, inositol should be present at a level of no greater than about 42 mg/100 kcal. In still other embodiments, the nutritional composition comprises inositol at a level of about 12 mg/100 kcal to about 40 mg/100 kcal. In a further embodiment, inositol is present in the nutritional composition at a level of about 17 mg/100 kcal to about 37 mg/100 kcal. Moreover, inositol can be present as exogenous inositol or inherent inositol. In embodiments, a major fraction of the inositol (i.e., at least 40%) is exogenous inositol. In certain embodiments, the ratio of exogenous to inherent inositol is at least 50:50; in other embodiments, the ratio of exogenous to inherent inositol is at least 65:35. In still other embodiments, the ratio of exogenous inositol to inherent inositol in the disclosed nutritional composition is at least 75:25.

In some embodiments, the nutritional composition(s) of the disclosure may also comprise at least one protein or protein equivalent source, which can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins may be partially hydrolyzed or extensively hydrolyzed. In still other embodiments, the protein equivalent source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 20% to about 80%, or from about 30% to about 80%, or even from about 40% to about 60%.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed. The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

In a particular embodiment, the nutritional composition is protein-free and contains free amino acids as a protein equivalent source. In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 kcal. In an embodiment, 100% of the free amino acids have a molecular weight of less than 500 Daltons. In this embodiment, the nutritional formulation may be hypoallergenic.

In an embodiment, the protein source comprises from about 40% to about 85% whey protein and from about 15% to about 60% casein.

In some embodiments, the nutritional composition comprises no greater than 7 g/100 kcal, and, in certain embodiments, between about 1 g and about 7 g of a protein and/or protein equivalent source per 100 kcal. In other embodiments, the nutritional composition comprises between about 3.5 g and about 4.5 g of protein or protein equivalent per 100 kcal.

In some embodiments, the nutritional composition comprises at least one carbohydrate source. Carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can be greater than 5 g/100 kcal; in some embodiments, it can vary from between about 5 g and about 25 g/100 kcal. In some embodiments, the amount of carbohydrate is between about 6 g and about 22 g/100 kcal. In other embodiments, the amount of carbohydrate is between about 12 g and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

In one particular embodiment, the carbohydrate component of the nutritional composition is comprised of 100% lactose. In another embodiment, the additional carbohydrate component comprises between about 0% and 60% lactose. In another embodiment, the carbohydrate component comprises between about 15% and 55% lactose. In yet another embodiment, the carbohydrate component comprises between about 20% and 30% lactose. In these embodiments, the remaining source of carbohydrates may be any carbohydrate known in the art. In an embodiment, the carbohydrate component comprises about 25% lactose and about 75% corn syrup solids.

In some embodiments, the carbohydrate may comprise at least one starch or starch component. A starch is a carbohydrate composed of two distinct polymer fractions: amylose and amylopectin. Amylose is the linear fraction consisting of α-1,4 linked glucose units. Amylopectin has the same structure as amylose, but some of the glucose units are combined in an α-1,6 linkage, giving rise to a branched structure. Starches generally contain 17-24% amylose and from 76-83% amylopectin. Yet special genetic varieties of plants have been developed that produce starch with unusual amylose to amylopectin ratios. Some plants produce starch that is free of amylose. These mutants produce starch granules in the endosperm and pollen that stain red with iodine and that contain nearly 100% amylopectin. Predominant among such amylopectin producing plants are waxy corn, waxy sorghum and waxy rice starch.

The performance of starches under conditions of heat, shear and acid may be modified or improved by chemical modifications. Modifications are usually attained by introduction of substituent chemical groups. For example, viscosity at high temperatures or high shear can be increased or stabilized by cross-linking with di- or polyfunctional reagents, such as phosphorus oxychloride.

In some instances, the nutritional compositions of the present disclosure comprise at least one starch that is gelatinized or pregelatinized. As is known in the art, gelatinization occurs when polymer molecules interact over a portion of their length to form a network that entraps solvent and/or solute molecules. Moreover, gels form when pectin molecules lose some water of hydration owing to competitive hydration of cosolute molecules. Factors that influence the occurrence of gelation include pH, concentration of cosolutes, concentration and type of cations, temperature and pectin concentration. Notably, LM pectin will gel only in the presence of divalent cations, such as calcium ions. And among LM pectins, those with the lowest degree of esterification have the highest gelling temperatures and the greatest need for divalent cations for crossbridging.

Meanwhile, pregelatinization of starch is a process of precooking starch to produce material that hydrates and swells in cold water. The precooked starch is then dried, for example by drum drying or spray drying. Moreover the starch of the present disclosure can be chemically modified to further extend the range of its finished properties. The nutritional compositions of the present disclosure may comprise at least one pregelatinized starch.

Native starch granules are insoluble in water, but, when heated in water, native starch granules begin to swell when sufficient heat energy is present to overcome the bonding forces of the starch molecules. With continued heating, the granule swells to many times its original volume. The friction between these swollen granules is the major factor that contributes to starch paste viscosity.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose, rice starch comprises an amylose:amylopectin ratio of about 20:80, and waxy rice starch comprises only about 2% amylose. Further, tapioca starch generally comprises about 15% to about 18% amylose, and wheat starch has an amylose content of around 25%.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Suitable fats or lipids for use in the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The amount of lipids or fats is, in one embodiment, no greater than about 7 g/100 kcal; in some embodiments, the lipid or fat is present at a level of from about 2 to about 7 g/100 kcal.

The nutritional composition may also contain one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose (PDX), polydextrose powder, lactulose, lactosucrose, raffinose, gluco-oligosaccharide, inulin, fructo-oligosaccharide (FOS), isomalto-oligosaccharide, soybean oligosaccharides, lactosucrose, xylo-oligosaccharide (XOS), chito-oligosaccharide, manno-oligosaccharide, aribino-oligosaccharide, siallyl-oligosaccharide, fuco-oligosaccharide, galacto-oligosaccharides (GOS) and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.01 g/100 kcal to about 1.5 g/100 kcal. In certain embodiments, the total amount of prebiotics present in the nutritional composition may be from about 0.15 g/100 kcal to about 1.5 g/100 kcal. Moreover, the nutritional composition may comprise a prebiotic component comprising PDX. In some embodiments, the prebiotic component comprises at least 20% w/w PDX, GOS or a mixture thereof.

The amount of PDX in the nutritional composition may, in an embodiment, be within the range of from about 0.015 g/100 kcal to about 1.5 g/100 kcal. In another embodiment, the amount of polydextrose is within the range of from about 0.2 g/100 kcal to about 0.6 g/100 kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.05 g/100 kcal to about 1.5 g/100 kcal.

The prebiotic component also comprises GOS in some embodiments. The amount of GOS in the nutritional composition may, in an embodiment, be from about 0.015 g/100 kcal to about 1.0 g/100 kcal. In another embodiment, the amount of GOS in the nutritional composition may be from about 0.2 g/100 kcal to about 0.5 g/100 kcal.

In a particular embodiment of the present disclosure, PDX is administered in combination with GOS.

In a particular embodiment, GOS and PDX are supplemented into the nutritional composition in a total amount of at least about 0.015 g/100 kcal or about 0.015 g/100 kcal to about 1.5 mg/100 kcal. In some embodiments, the nutritional composition may comprise GOS and PDX in a total amount of from about 0.1 to about 1.0 mg/100 kcal.

Lactoferrin can also included in some embodiments of the nutritional composition of the present disclosure. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) and 28 to 31 (RKVR) are arginine-rich cationic domains in the N-terminus especially critical to the antimicrobial activities of lactoferrin. A similar region in the N-terminus is found in bovine lactoferrin (residues 17 to 42; FKCRRWQWRMKKLGAPSITCVRRAFA).

Lactoferrins from different host species may vary in their amino acid sequences though commonly possess a relatively high isoelectric point with positively charged amino acids at the end terminal region of the internal lobe. Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 55% homology with human lactoferrin and in some embodiments, at least 65% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

In one embodiment, lactoferrin is present in the nutritional composition in an amount of at least about 15 mg/100 kCal. In certain embodiments, the nutritional composition may include between about 15 and about 300 mg lactoferrin per 100 kCal. In another embodiment, where the nutritional composition is an infant formula, the nutritional composition may comprise lactoferrin in an amount of from about 60 mg to about 150 mg lactoferrin per 100 kCal; in yet another embodiment, the nutritional composition may comprise about 60 mg to about 100 mg lactoferrin per 100 kCal.

In some embodiments, the nutritional composition can include lactoferrin in the quantities of from about 0.5 mg to about 1.5 mg per milliliter of formula. In nutritional compositions replacing human milk, lactoferrin may be present in quantities of from about 0.6 mg to about 1.3 mg per milliliter of formula. In certain embodiments, the nutritional composition may comprise between about 0.1 and about 2 grams lactoferrin per liter. In some embodiments, the nutritional composition includes between about 0.6 and about 1.5 grams lactoferrin per liter of formula.

The bLF that is used in certain embodiments may be any bLF isolated from whole milk and/or having a low somatic cell count, wherein "low somatic cell count" refers to a somatic cell count less than 200,000 cells/mL. By way of example, suitable bLF is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

The nutritional composition of the disclosure can also contain a source of LCPUFAs in certain embodiments; especially a source of LCPUFAs that comprises DHA. Other suitable LCPUFAs include, but are not limited to, α-linoleic acid, γ-linoleic acid, linoleic acid, linolenic acid, eicosapentaenoic acid (EPA) and ARA. Indeed, DHA and/or ARA may act synergistically with inositol to further improve neurological health and development.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The amount of long chain polyunsaturated fatty acid in the nutritional composition is advantageously at least about 5 mg/100 kcal, and may vary from about 5 mg/100 kcal to about 100 mg/100 kcal, more preferably from about 10 mg/100 kcal to about 50 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

In some embodiments the nutritional composition may include an enriched lipid fraction derived from milk. The enriched lipid fraction derived from milk may be produced by any number of fractionation techniques. These techniques include but are not limited to melting point fractionation, organic solvent fractionation, super critical fluid fractionation, and any variants and combinations thereof. In some embodiments the nutritional composition may include an enriched lipid fraction derived from milk that contains milk fat globules.

In certain embodiments, the addition of the enriched lipid fraction or the enriched lipid fraction including milk fat globules may provide a source of saturated fatty acids, trans-fatty acids, monounsaturated fatty acids, polyunsaturated fatty acids, OBCFAs, BCFAs, CLA, cholesterol, phospholipids, and/or milk fat globule membrane proteins to the nutritional composition.

The milk fat globules may have an average diameter (volume-surface area average diameter) of at least about 2 μm. In some embodiments, the average diameter is in the range of from about 2 μm to about 13 μm. In other embodiments, the milk fat globules may range from about 2.5 μm to about 10 μm. Still in other embodiments, the milk fat globules may range in average diameter from about 3 μm to about 6 μm. The specific surface area of the globules is, in certain embodiments, less than 3.5 $m^2/g$, and in other embodiments is between about 0.9 $m^2/g$ to about 3 $m^2/g$. Without being bound by any particular theory, it is believed that milk fat globules of the aforementioned sizes are more accessible to lipases therefore leading to better digestion lipid digestion.

In some embodiments the enriched lipid fraction and/or milk fat globules contain saturated fatty acids. The saturated fatty acids may be present in a concentration from about 0.1 g/100 kcal to about 8.0 g/100 kcal. In certain embodiments the saturated fatty acids may be present from about 0.5 g/100 kcal to about 2.0 g/100 kcal. In still other embodiments the saturated fatty acids may be present from about 3.5 g/100 kcal to about 6.9 g/100 kcal.

Examples of saturated fatty acids suitable for inclusion include, but are not limited to, butyric, valeric, caproic, caprylic, decanoic, lauric, myristic, palmitic, steraic, arachidic, behenic, alignoceric, tetradecanoic, hexadecanoic, palmitic, and octadecanoic acid, and/or combinations and mixtures thereof.

Additionally, the enriched lipid fraction and/or milk fat globules may comprise, in some embodiments, lauric acid. Lauric acid, also known as dodecanoic acid, is a saturated fatty acid with a 12-carbon atom chain and is believed to be one of the main antiviral and antibacterial substances currently found in human breast milk. The milk fat globules may be enriched with triglycerides containing lauric acid at either the Sn-1, Sn-2 and/or Sn-3 positions. Without being bound by any particular theory, it is believed that when the enriched lipid fraction is ingested, the mouth lingual lipase and pancreatic lipase will hydrolyze the triglycerides to a mixture of glycerides including mono-lauric and free lauric acid.

The concentration of lauric acid in the globules varies from 80 mg/100 ml to 800 mg/100 ml. The concentration of monolauryl n the globules can be in the range of 20 mg/100 ml to 300 mg/100 ml feed. In some embodiments, the range is 60 mg/100 ml to 130 mg/100 ml.

The enriched lipid fraction and/or milk fat globules may contain trans-fatty acids in certain embodiments. The trans-fatty acids included in the milk fat globules may be monounsaturated or polyunsaturated trans-fatty acids. In some embodiments the trans-fatty acids may be present in an amount from about 0.2 g/100 kcal to about 7.0 g/100 kcal. In other embodiments the trans-fatty acids may be present in an amount from about 3.4 g/100 kcal to about 5.2 g/100 kcal. In yet other embodiments the trans-fatty acids may be present from about 1.2 g/100 kcal to about 4.3 g/100 kcal.

Examples of trans-fatty acids for inclusion include, but are not limited to, vaccenic, or elaidic acid, and mixtures thereof. Moreover, when consumed, mammals convert vaccenic acid into rumenic acid, which is a conjugated linoleic acid that exhibits anticarcinogenic properties. Additionally, a diet enriched with vaccenic acid may help lower total cholesterol, LDL cholesterol and triglyceride levels.

In some embodiments the enriched lipid fraction and/or milk fat globules may contain OBCFAs. In certain embodiments, the OBCFAs may be present in an amount from about 0.3 g/100 kcal to about 6.1 g/100 kcal. In other embodiments OBCFAs may be present in an amount from about 2.2 g/100 kcal to about 4.3 g/100 kcal. In yet another embodiment OBCFAs may be present in an amount from about 3.5 g/100 kcal to about 5.7 g/100 kcal. In still other embodiments, the milk fat globules comprise at least one OBCFA.

Typically, an infant may absorb OBCFAs while in utero and from the breast milk of a nursing mother. Therefore, OBCFAs that are identified in human milk are preferred for inclusion in the milk fat globules of the nutritional composition. Addition of OBCFAs to infant or children's formulas allows such formulas to mirror the composition and functionality of human milk and to promote general health and well-being.

In some embodiments, the enriched lipid fraction and/or milk fat globules may comprise BCFAs. In some embodiments the BCFAs are present at a concentration from about 0.2 g/100 kcal and about 5.82 g/100 kcal. In another embodiment, the BCFAs are present in an amount of from about 2.3 g/100 kcal to about 4.2 g/100 kcal. In yet another embodiment the BCFAs are present from about 4.2 g/100 kcal to about 5.82 g/100 kcal. In still other embodiments, the milk fat globules comprise at least one BCFA.

BCFAs that are identified in human milk are preferred for inclusion in the nutritional composition. Addition of BCFAs to infant or children's formulas allows such formulas to mirror the composition and functionality of human milk and to promote general health and well-being.

In certain embodiments the enriched lipid fraction and/or milk fat globules may comprise CLA. In some embodiments CLA may be present in a concentration from about 0.4 g/100 kcal to about 2.5 g/100 kcal. In other embodiments CLA may be present from about 0.8 g/100 kcal to about 1.2 g/100 kcal. In yet other embodiments CLA may be present from about 1.2 g/100 kcal to about 2.3 g/100 kcal. In still other embodiments, the milk fat globules comprise at least one CLA.

CLAs that are identified in human milk are preferred for inclusion in the nutritional composition. Typically, CLAs are absorbed by the infant from the human milk of a nursing mother. Addition of CLAs to infant or children's formulas allows such formulas to mirror the composition and functionality of human milk and to promote general health and wellbeing.

Examples of CLAs found in the milk fat globules for the nutritional composition include, but are not limited to, cis-9, trans-11 CLA, trans-10, cis-12 CLA, cis-9, trans-12 octadecadienoic acid, and mixtures thereof.

The enriched lipid fraction and/or milk fat globules of the present disclosure comprise monounsaturated fatty acids in some embodiments. The enriched lipid fraction and/or milk fat globules may be formulated to include monounsaturated fatty acids from about 0.8 g/100 kcal to about 2.5 g/100 kcal. In other embodiments the milk fat globules may include monounsaturated fatty acids from about 1.2 g/100 kcal to about 1.8 g/100 kcal.

Examples of monounsaturated fatty acids suitable include, but are not limited to, palmitoleic acid, cis-vaccenic acid, oleic acid, and mixtures thereof.

In certain embodiments, the enriched lipid fraction and/or milk fat globules of the present disclosure comprise polyunsaturated fatty acids from about 2.3 g/100 kcal to about 4.4 g/100 kcal. In other embodiments, the polyunsaturated fatty acids are present from about 2.7 g/100 kcal to about 3.5 g/100 kcal. In yet another embodiment, the polyunsaturated fatty acids are present from about 2.4 g/100 kcal to about 3.3 g/100 kcal.

In some embodiments, the enriched lipid fraction and/or milk fat globules of the present disclosure comprise polyunsaturated fatty acids, such as, for example linoleic acid, linolenic acid, octadecatrienoic acid, arachidonic acid (ARA), eicosatetraenoic acid, eicopsapentaenoic acid (EPA), docosapentaenoic acid (DPA), and docosahexaenoic acid (DHA). Polyunsaturated fatty acids are the precursors for prostaglandins and eicosanoids, which are known to provide numerous health benefits, including, anti-inflammatory response, cholesterol absorption, and increased bronchial function.

The enriched lipid fraction and/or milk fat globules of the present disclosure can also comprise cholesterol in some embodiments from about 100 mg/100 kcal to about 400 mg/100 kcal. In another embodiment, cholesterol is present from about 200 mg/100 kcal to about 300 mg/100 kcal. As is similar to human milk and bovine milk, the cholesterol included in the milk fat globules may be present in the outer bilayer membrane of the milk fat globule to provide stability to the globular membrane.

In some embodiments, the enriched lipid fraction and/or milk fat globules of the present disclosure comprise phospholipids from about 50 mg/100 kcal to about 200 mg/100 kcal. In other embodiments, the phospholipids are present from about 75 mg/100 kcal to about 150 mg/100 kcal. In yet other embodiments, the phospholipids are present at a concentration of from about 100 mg/100 kcal to about 250 mg/100 kcal.

In certain embodiments, phospholipids may be incorporated into the milk fat globules to stabilize the milk fat globule by providing a phospholipid membrane or bilayer phospholipid membrane. Therefore, in some embodiments the milk fat globules may be formulated with higher amounts of phospholipids than those found in human milk. The phospholipid composition of human milk lipids, as the weight percent of total phospholipids, is phosphatidylcholine ("PC") 24.9%, phosphatidylethanolamine ("PE") 27.7%, phosphatidylserine ("PS") 9.3%, phosphatidylinositol ("PI") 5.4%, and sphingomyelin ("SPM") 32.4%, (Harzer, G. et al., Am. J. Clin. Nutr., Vol. 37, pp. 612-621 (1983)). Thus in one embodiment, the milk fat globules comprise one or more of PC, PE, PS, PI, SPM, and mixtures thereof. Further, the phospholipid composition included in the milk fat globules may be formulated to provide certain health benefits by incorporating desired phospholipids.

In certain embodiments, the enriched lipid fraction and/or milk fat globules of the present disclosure comprise milk fat globule membrane protein. In some embodiments, the milk fat globule membrane protein is present from about 50 mg/100 kcal to about 500 mg/100 kcal.

Galactolipids may be included, in some embodiments, in the enriched lipid fraction and/or milk fat globules of the present disclosure. For purposes of this disclosure "galactolipids" refer to any glycolipid whose sugar group is galactose. More specifically, galactolipids differ from glycosphingolipids in that they do not have nitrogen in their composition. Galactolipids play an important role in supporting brain development and overall neuronal health. Additionally, the galactolipids, galactocerebroside and sulfatides constitute about 23% and 4% of total myelin lipid content respectively, and thus may be incorporated into the milk fat globules in some embodiments.

Additionally, the nutritional compositions of the present disclosure comprise at least one source of pectin. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counterions.

Moreover, pectin has a unique ability to form gels. Generally, under similar conditions, a pectin's degree of gelation, the gelling temperature, and the gel strength are proportional to one another, and each is generally proportional to the molecular weight of the pectin and inversely proportional to the degree of esterification. For example, as the pH of a pectin solution is lowered, ionization of the carboxylate groups is repressed, and, as a result of losing their charge, saccharide molecules do not repel each other over their entire length. Accordingly, the polysaccharide molecules can associate over a portion of their length to form a gel. Yet pectins with increasing degrees of methylation will gel at somewhat higher pH because they have fewer carboxylate anions at any given pH. (J. N. Bemiller, *An Introduction to Pectins: Structure and Properties*, Chemistry and Function of Pectins; Chapter 1; 1986.)

The nutritional composition may comprise a gelatinized and/or pregelatinized starch together with pectin and/or gelatinized pectin. While not wishing to be bound by this or any other theory, it is believed that the use of pectin, such as LM pectin, which is a hydrocolloid of large molecular weight, together with starch granules, provides a synergistic effect that increases the molecular internal friction within a fluid matrix. The carboxylic groups of the pectin may also interact with calcium ions present in the nutritional composition, thus leading to an increase in viscosity, as the carboxylic groups of the pectin form a weak gel structure with the calcium ion(s), and also with peptides present in the nutritional composition. In some embodiments, the nutritional composition comprises a ratio of starch to pectin that is between about 12:1 and 20:1, respectively. In other embodiments, the ratio of starch to pectin is about 17:1. In some embodiments, the nutritional composition may comprise between about 0.05 and about 2.0% w/w pectin. In a particular embodiment, the nutritional composition may comprise about 0.5% w/w pectin.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

The nutritional composition may contain at least one acidic polysaccharide. An acidic polysaccharide, such as negatively charged pectin, may induce an anti-adhesive effect on pathogens in a subject's gastrointestinal tract. Indeed, nonhuman milk acidic oligosaccharides derived from pectin are able to interact with the epithelial surface and are known to inhibit the adhesion of pathogens on the epithelial surface.

In some embodiments, the nutritional composition comprises at least one pectin-derived acidic oligosaccharide. Pectin-derived acidic oligosaccharide(s) (pAOS) result from enzymatic pectinolysis, and the size of a pAOS depends on the enzyme use and on the duration of the reaction. In such embodiments, the pAOS may beneficially affect a subject's stool viscosity, stool frequency, stool pH and/or feeding tolerance. The nutritional composition of the present disclosure may comprise between about 2 g pAOS per liter of formula and about 6 g pAOS per liter of formula. In an embodiment, the nutritional composition comprises about 0.2 g pAOS/dL, corresponding to the concentration of acidic oligosaccharides in human milk. (Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, August 2005)

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids are found in milk, such as bovine and caprine. In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 kcals to about 45 mg/100 kcal. In some embodiments sialic acid may be present in an amount from about 5 mg/100 kcals to about 30 mg/100 kcals. In still other embodiments, sialic acid may be present in an amount from about 10 mg/100 kcals to about 25 mg/100 kcals.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (LGG) (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{12}$ cfu of probiotic(s) per 100 kcal. In some embodiments the amount of probiotic may be from about $1\times10^6$ to about $1\times10^9$ cfu of probiotic(s) per 100 kcal. In certain other embodiments the amount of probitic may vary from about $1\times10^7$ cfu/100 kcal to about $1\times10^8$ cfu of probiotic(s) per 100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents, which refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc. In non-viable probiotics are included in the nutritional composition, the amount of the probiotic cell equivalents may vary from about $1\times10^4$ to about $1.5\times10^{10}$ cell equivalents of probiotic(s) per 100 kcal. In some embodiments the amount of probiotic cell equivalents may be from about $1\times10^6$ to about $1\times10^9$ cell equivalents of probiotic(s) per 100 kcal nutritional composition. In certain other embodiments the amount of probiotic cell equivalents may vary from about $1\times10^7$ to about $1\times10^8$ cell equivalents of probiotic(s) per 100 kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅘ of the time elapsed in the exponential phase.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan present in the composition is at between about 0.010 and about 0.080 g per 100 g of composition. In other embodiments, the nutritional composition comprises between about 10 and about 30 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg β-glucan per day. The nutritional composition may be delivered in multiple doses to reach a target amount of β-glucan delivered to the subject throughout the day.

In some embodiments, the amount of β-glucan in the nutritional composition is between about 3 mg and about 17 mg per 100 kcal. In another embodiment the amount of β-glucan is between about 6 mg and about 17 mg per 100 kcal.

The nutritional composition of this disclosure may also include phosphatidylethanolamine ("PE"), recognized as having neurogenesis-promoting effects, particularly in infants, as taught by Ser. No. 13/739,787, filed Jan. 11, 2013. It is believed that PE may synergistically work with inositol to enhance the effects noted herein. Examples of PE suitable for inclusion in the neurologic component include, but are not limited to, 1,2-Dierucoyl-sn-glycero-3-phosphoethanolamine, 1,2-Dilauroyl-sn-glycero-3-phosphoethanolamine, 1,2-Dimyristoyl-sn-glycero-3-phosphoethanolamine, 1,2-Dioleoyl-sn-glycero-3-phosphoethanolamine, 1,2-Dipalmitoyl-sn-glycero-3-phosphoethanolamine, 1,2-Distearoyl-sn-glycero-3-phosphoethanolamine, 1-Palmitoyl-2-oleoyl-sn-glycero-3-phosphoethanolamine, 1-arachidonoyl-2-stearoyl-sn-glycerol 3-phospho ethanolamine, N,1-Diarachidonoyl-2-stearoyl-sn-glycerol 3-phosphoethanolamine, and phosphoethanolanime containing any fatty acid at the 1 and/or 2 positions.

PE may be present, in some embodiments, in an amount from about 3.7 mg/100 kcal to about 37 mg/100 kcal. In other embodiments, PE may be present from about 10 mg/100 kcal to about 30 mg/100 kcal. In still other embodiments, PE may be present from about 15 mg/100 kcal to about 25 mg/100 kcal.

Sphingomyelin has also been recognized as having neurogenesis-promoting effects, particularly in infants, as taught by Ser. No. 13/739,787, filed Jan. 11, 2013, and can be incorporated into the nutritional composition of the present disclosure in certain embodiments, to synergistically combine with inositol to further improve the disclosed neurological benefits. Sphingomyelin refers to a class of sphingolipids found in animal cell membranes, particularly in the myelin sheath that surrounds nervous cell axons. In humans, sphingomyelin typically makes up 10% to 20% of plasma membrane lipids. It is believed that sphingomyelin serves to electrically insulate nerve cell axons as it makes up 25% the total lipids in the myelin sheath that surround and insulate cells of the central nervous system. Membrane sphingomyelin is the precursor for sphingosine which is the precursor for sphingosine-1-phosphate, which may have a role in neurogenesis and is neuroprotective. Sphingosine-1-phosphate may also facilitate neural stem/progenitor cell ("NSPC") migration, which is essential to the development of the nervous system as well as the ongoing neurogenesis that occurs in the mature central nervous system.

Examples of sphingomyelin suitable for inclusion in the neurologic component of the nutritional composition include, but are not limited to ceramide phosphorylcholine and ceramide phosphorylethanolamine, N-oleoyl sphingomyelin, N-stearoyl sphingomyelin, and/or D-erythro N-palmitoyl sphingomyelin, and mixtures thereof. For example, in one embodiment the sphingomyelin included in the neurologic component may be synthetic sphingomyelin prepared according to the procedures of U.S. Pat. No. 7,687,652 to Rochlin et al., however, the present disclosure can also include other processes for production of synthetic sphingomyelin.

When present, sphingomyelin can be incorporated at a level of about 0.15 mg/100 kcal to about 73 mg/100 kcal.

Alpha-lipoic acid (ALA) can also be incorporated into the nutritional composition of the present disclosure in some embodiments. ALA has been recognized as having neurogenesis-promoting effects, particularly in infants, as taught by Ser. No. 13/942,794, filed Jul. 16, 2013. ALA may, under certain circumstances, synergistically combine with inositol to further improve the neurological benefits of inositol. Examples of ALA suitable for use herein include, but are not limited to, enantiomers and racemic mixtures of ALA, including, R-lipoic acid "RLA", S-lipoic acid "SLA", and R/S-LA. Also suitable is R-lipoic acid stabilized with either sodium ("Na-RALA") or potassium as Potassium-R-Lipoate.

When incorporated into the disclosed nutritional composition, ALA may be present, in some embodiments, in an amount from about 0.1 mg/100 kcal to about 35 mg/100 kcal. In some embodiments, ALA may be present in an amount from about 2.0 mg/100 kcal to about 25 mg/100 kcal. In still other embodiments, ALA may be present in an amount from about 5.0 mg/100 kcal to about 15 mg/100 kcal.

In certain embodiments, the nutritional composition of the present disclosure further comprises epigallocatchin-gallate (EGCG), which has been recognized as having neurogenesis-promoting effects, particularly in infants, as taught by Ser. No. 14/044,913, filed Oct. 3, 2013. It is believed that EGCG may synergistically combine with inositol to further improve the neurological benefits of inositol, especially when EGCG is present in the disclosed nutritional composition at a level of about 5 mg/100 kcal to about 120 mg/100 kcal.

Sulforaphane, which includes L-sulforaphane, may be incorporated into the nutritional composition in an amount from about 1.5 mg/100 kcal to about 7.5 mg/100 kcal. Still in some embodiments, sulforaphane may be present in an amount from about 2 mg/100 kcal to about 6 mg/100 kcal. In some embodiments, sulforaphane may be present in an amount from about 3 mg/100 kcal to about 5 mg/100 kcal. Sulforaphane has been recognized as having neurogenesis-promoting effects, particularly in infants, as taught by Ser. No. 13/942,794, filed Jul. 16, 2013, and may also exhibit synergy with inositol herein.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 300 µm.

If the nutritional composition is in the form of a ready-to-use product, the osmolality of the nutritional composition may be between about 100 and about 1100 mOsm/kg water, more typically about 200 to about 700 mOsm/kg water.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 kcal. The amount of protein typically can vary from about 1 to about 7 g/100 kcal. The amount of carbohydrate typically can vary from about 6 to about 22 g/100 kcal.

The nutritional composition of the present disclosure may further include at least one additional phytonutrient, that is, another phytonutrient component in addition to the pectin and/or starch components described hereinabove. Phytonutrients, or their derivatives, conjugated forms or precursors, that are identified in human milk are preferred for inclusion in the nutritional composition. Typically, dietary sources of carotenoids and polyphenols are absorbed by a nursing mother and retained in milk, making them available to nursing infants. Addition of these phytonutrients to infant or children's formulas allows such formulas to mirror the composition and functionality of human milk and to promote general health and well being.

For example, in some embodiments, the nutritional composition of the present disclosure may comprise, in an 8 fl. oz. (236.6 mL) serving, between about 80 and about 300 mg anthocyanins, between about 100 and about 600 mg proanthocyanidins, between about 50 and about 500 mg flavan-3-ols, or any combination or mixture thereof. In other embodiments, the nutritional composition comprises apple extract, grape seed extract, or a combination or mixture thereof. Further, the at least one phytonutrient of the nutritional composition may be derived from any single or blend of fruit, grape seed and/or apple or tea extract(s).

For the purposes of this disclosure, additional phytonutrients may be added to a nutritional composition in native, purified, encapsulated and/or chemically or enzymatically-modified form so as to deliver the desired sensory and stability properties. In the case of encapsulation, it is desirable that the encapsulated phytonutrients resist dissolution with water but are released upon reaching the small intestine. This could be achieved by the application of enteric coatings, such as cross-linked alginate and others.

Examples of additional phytonutrients suitable for the nutritional composition include, but are not limited to, anthocyanins, proanthocyanidins, flavan-3-ols (i.e. catechins, epicatechins, etc.), flavanones, flavonoids, isoflavonoids, stilbenoids (i.e. resveratrol, etc.)proanthocyanidins, anthocyanins, resveratrol, quercetin, curcumin, and/or any mixture thereof, as well as any possible combination of phytonutrients in a purified or natural form. Certain components, especially plant-based components of the nutritional compositions may provide a source of phytonutrients.

Some amounts of phytonutrients may be inherently present in known ingredients, such as natural oils, that are commonly used to make nutritional compositions for pediatric subjects. These inherent phytonutrient(s) may be but are not necessarily considered part of the phytonutrient component described in the present disclosure. In some embodiments, the phytonutrient concentrations and ratios as described herein are calculated based upon added and inherent phytonutrient sources. In other embodiments, the phytonutrient concentrations and ratios as described herein are calculated based only upon added phytonutrient sources.

In some embodiments, the nutritional composition comprises anthocyanins, such as, for example, glucosides of aurantinidin, cyanidin, delphinidin, europinidin, luteolinidin, pelargonidin, malvidin, peonidin, petunidin, and rosinidin. These and other anthocyanins suitable for use in the nutritional composition are found in a variety of plant sources. Anthocyanins may be derived from a single plant source or a combination of plant sources. Non-limiting examples of plants rich in anthocyanins suitable for use in the inventive composition include: berries (acai, grape, bilberry, blueberry, lingonberry, black currant, chokeberry, blackberry, raspberry, cherry, red currant, cranberry, crowberry, cloudberry, whortleberry, rowanberry), purple corn, purple potato, purple carrot, red sweet potato, red cabbage, eggplant.

In some embodiments, the nutritional composition of the present disclosure comprises proanthocyanidins, which include but are not limited to flavan-3-ols and polymers of flavan-3-ols (e.g., catechins, epicatechins) with degrees of polymerization in the range of 2 to 11. Such compounds may be derived from a single plant source or a combination of plant sources. Non-limiting examples of plant sources rich in proanthocyanidins suitable for use in the disclosed nutritional composition include: grape, grape skin, grape seed, green tea, black tea, apple, pine bark, cinnamon, cocoa, bilberry, cranberry, black currant chokeberry.

Non-limiting examples of flavan-3-ols which are suitable for use in the disclosed nutritional composition include catechin, epicatechin, gallocatechin, epigallocatechin, epicatechin gallate, epicatechin-3-gallate, epigallocatechin and gallate. Plants rich in the suitable flavan-3-ols include, but are not limited to, teas, red grapes, cocoa, green tea, apricot and apple.

Certain polyphenol compounds, in particular flavan-3-ols, may improve learning and memory in a human subject by increasing brain blood flow, which is associated with an increase and sustained brain energy/nutrient delivery as well as formation of new neurons. Polyphenols may also provide neuroprotective actions and may increase both brain synaptogenesis and antioxidant capability, thereby supporting optimal brain development in younger children.

Preferred sources of flavan-3-ols for the nutritional composition include at least one apple extract, at least one grape seed extract or a mixture thereof. For apple extracts, flavan-3-ols are broken down into monomers occurring in the range 4% to 20% and polymers in the range 80% to 96%. For grape seed extracts flavan-3-ols are broken down into monomers (about 46%) and polymers (about 54%) of the total favan-3-ols and total polyphenolic content. Preferred degree of polymerization of polymeric flavan-3-ols is in the range of between about 2 and 11. Furthermore, apple and grape seed extracts may contain catechin, epicatechin, epigallocatechin, epicatechin gallate, epigallocatechin gallate, polymeric proanthocyanidins, stilbenoids (i.e. resveratrol), flavonols (i.e. quercetin, myricetin), or any mixture thereof. Plant sources rich in flavan-3-ols include, but are not limited to apple, grape seed, grape, grape skin, tea (green or black), pine bark, cinnamon, cocoa, bilberry, cranberry, black currant, chokeberry.

If the nutritional composition is administered to a pediatric subject, an amount of flavan-3-ols, including monomeric flavan-3-ols, polymeric flavan-3-ols or a combination thereof, ranging from between about 0.01 mg and about 450 mg per day may be administered. In some cases, the amount of flavan-3-ols administered to an infant or child may range from about 0.01 mg to about 170 mg per day, from about 50 to about 450 mg per day, or from about 100 mg to about 300 mg per day.

In an embodiment of the disclosure, flavan-3-ols are present in the nutritional composition in an amount ranging from about 0.4 to about 3.8 mg/g nutritional composition (about 9 to about 90 mg/100 kcal). In another embodiment, flavan-3-ols are present in an amount ranging from about 0.8 to about 2.5 mg/g nutritional composition (about 20 to about 60 mg/100 kcal).

In some embodiments, the nutritional composition of the present disclosure comprises flavanones. Non-limiting examples of suitable flavanones include butin, eriodictyol, hesperetin, hesperidin, homeriodictyol, isosakuranetin, naringenin, naringin, pinocembrin, poncirin, sakuranetin, sakuranin, steurbin. Plant sources rich in flavanones include, but are not limited to orange, tangerine, grapefruit, lemon, lime. The nutritional composition may be formulated to deliver between about 0.01 and about 150 mg flavanones per day.

Moreover, the nutritional composition may also comprise flavonols. Flavonols from plant or algae extracts may be used. Flavonols, such as ishrhametin, kaempferol, myricetin, quercetin, may be included in the nutritional composition in amounts sufficient to deliver between about 0.01 and 150 mg per day to a subject.

The phytonutrient component of the nutritional composition may also comprise phytonutrients that have been identified in human milk, including but not limited to naringenin, hesperetin, anthocyanins, quercetin, kaempferol, epicatechin, epigallocatechin, epicatechin-gallate, epigallocatechin-gallate or any combination thereof. In certain embodiments, the nutritional composition comprises between about 50 and about 2000 nmol/L epicatechin, between about 40 and about 2000 nmol/L epicatechin gallate, between about 100 and about 4000 nmol/L epigallocatechin gallate, between about 50 and about 2000 nmol/L naringenin, between about 5 and about 500 nmol/L kaempferol, between about 40 and about 4000 nmol/L hesperetin, between about 25 and about 2000 nmol/L anthocyanins, between about 25 and about 500 nmol/L quercetin, or a mixture thereof. Furthermore, the nutritional composition may comprise the metabolite(s) of a phytonutrient or of its parent compound, or it may comprise other classes of dietary phytonutrients, such as glucosinolate or sulforaphane.

In certain embodiments, the nutritional composition comprises carotenoids, such as lutein, zeaxanthin, astaxanthin, lycopene, beta-carotene, alpha-carotene, gamma-carotene, and/or beta-cryptoxanthin. Plant sources rich in carotenoids include, but are not limited to kiwi, grapes, citrus, tomatoes, watermelons, papayas and other red fruits, or dark greens, such as kale, spinach, turnip greens, collard greens, romaine lettuce, broccoli, zucchini, garden peas and Brussels sprouts, spinach, carrots.

Humans cannot synthesize carotenoids, but over 34 carotenoids have been identified in human breast milk, including isomers and metabolites of certain carotenoids. In addition to their presence in breast milk, dietary carotenoids, such as alpha and beta-carotene, lycopene, lutein, zeaxanthin, astaxanthin, and cryptoxanthin are present in serum of lactating women and breastfed infants. Carotenoids in general have been reported to improve cell-to-cell communication, promote immune function, support healthy respiratory health, protect skin from UV light damage, and have been linked to reduced risk of certain types of cancer, and all-cause mortality. Furthermore, dietary sources of carotenoids and/or polyphenols are absorbed by human subjects, accumulated and retained in breast milk, making them available to nursing infants. Thus, addition of phytonutrients to infant formulas or children's products would bring the formulas closer in composition and functionality to human milk.

Flavonoids, as a whole, may also be included in the nutritional composition, as flavonoids cannot be synthesized by humans. Moreover, flavonoids from plant or algae extracts may be useful in the monomer, dimer and/or polymer forms. In some embodiments, the nutritional composition comprises levels of the monomeric forms of flavonoids similar to those in human milk during the first three months of lactation. Although flavonoid aglycones (monomers) have been identified in human milk samples, the conjugated forms of flavonoids and/or their metabolites may also be useful in the nutritional composition. The flavonoids could be added in the following forms: free, glucuronides, methyl glucuronides, sulphates, and methyl sulphates.

The nutritional composition may also comprise isoflavonoids and/or isoflavones. Examples include, but are not limited to, genistein (genistin), daidzein (daidzin), glycitein, biochanin A, formononetin, coumestrol, irilone, orobol, pseudobaptigenin, anagyroidisoflavone A and B, calycosin, glycitein, irigenin, 5-O-methylgenistein, pratensein, prunetin, psi-tectorigenin, retusin, tectorigenin, iridin, ononin, puerarin, tectoridin, derrubone, luteone, wighteone, alpinumisoflavone, barbigerone, di-O-methylalpinumisoflavone, and 4'-methyl-alpinumisoflavone. Plant sources rich in isoflavonoids, include, but are not limited to, soybeans, psoralea, kudzu, lupine, fava, chick pea, alfalfa, legumes and peanuts. The nutritional composition may be formulated to deliver between about 0.01 and about 150 mg isoflavones and/or isoflavonoids per day.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure further provides a method for providing nutritional support to a subject. The method includes administering to the subject an effective amount of the nutritional composition of the present disclosure.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. Each nutritional composition comprises a hydrolyzed protein, at least one pre-gelatinized starch, and at least one pectin. In certain embodiments, the nutritional compositions of the feeding regimen may also include a source of long chain polyunsaturated fatty acid, at least one prebiotic, an iron source, a source of β-glucan, vitamins or minerals, lutein, zeaxanthin, or any other ingredient described hereinabove. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Example 1

Figure 2:
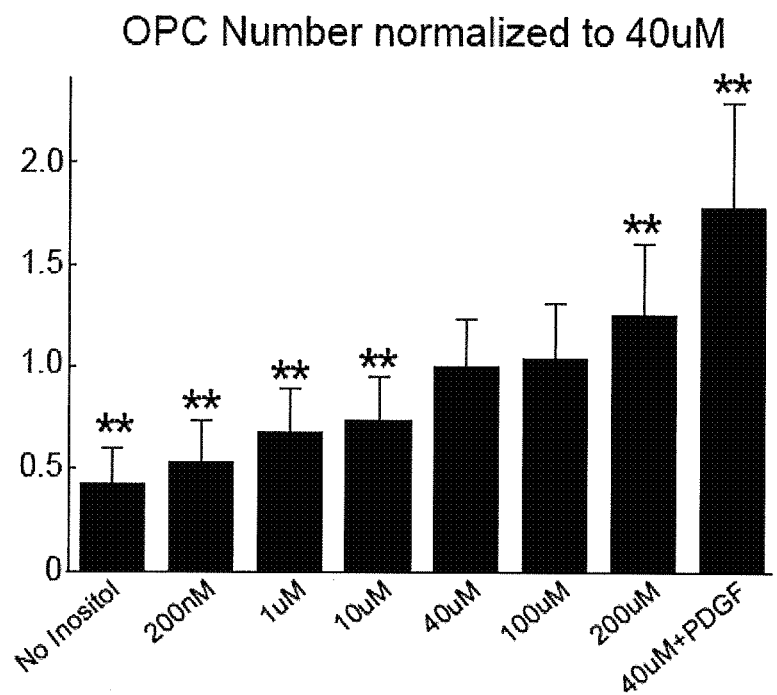
FIG. 2 illustrates the OPCs, normalized to 40 μM resulting from the testing of Example 2.
Figure 3:
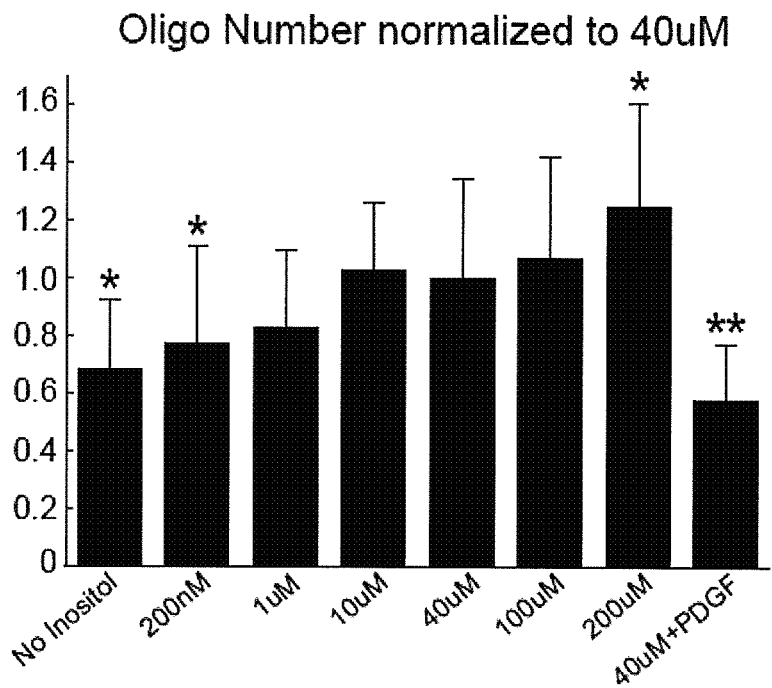
FIG. 3 illustrates the Oligo Number, normalized to 40 μM resulting from the testing of Example 3.

FIG. 1 illustrates the functional implications of inositol in oligodendroglia survival and proliferation. Inositol was added to purified oligodendroglial cultures and cells were analyzed for effects on proliferation, survival and differentiation by immunohistochemistry under the fluorescent microscopy. OPCs were analyzed by staining with antibody against PDGFRa and visualized in green fluorescence; and oligodendrocytes with that against MBP in red. As a result of the findings, inositol supplementation in purified oligodendroglia cultures significantly promotes oligodendroglial survival, resulting in a consistent increase in the number of oligodendrocyte precursor cells and mature oligodendrocytes (FIGS. 2 and 3). Depletion of inositol in the medium results in a fifty percent loss of oligodendrocyte precursor cells and thirty percent loss in oligodendrocytes. More importantly, the OPC and oligodendrocyte health significantly increased when supplemented with inositol at 200 μM compared to the 40 μM in the base medium.

Example 2

A culture condition containing 40 μM inositol in which the count of the numbers of living OPCs was normalized as 1, as a baseline control. The beginnings of culture of OPCs are equal in terms of OPC number in culture dish in all conditions. Inositol was added to each OPC culture at zero, 200 nM, 1 μM, 10 μM, 40 μM, 100 μM, and 200 μM. Since the OPCs only respond to platelet-derived growth factor PDGF, a potent mitogen, for proliferation, the condition containing 40 μM inositol and PDGF was set as a positive control. When compared to baseline control at 40 μM inositol, the quantification of OPCs were significantly decreased at zero, 200 nM, 1 μM and 10 μM ($*p<0.05$). Moreover, when increasing inositol to 200 μM, the OPCs number was significantly increased ($*p<0.05$). Such a positive effect reached about 70% of that in the positive control. The overall response to inositol displayed in a dose-dependent manner suggesting a true response to inositol. As a result of the findings, it concluded that nutritional supplementation of inositol significantly promotes oligodendroglial proliferation and survival. The results are graphically illustrated in FIG. 2

Example 3

As illustrated in FIG. 3, the 40 μM inositol level was set as a baseline control normalized as "1"; with the addition of PDGF a positive control for comparison. In the absence and the lower presence of inositol 200 nM, the quantification of Oligo numbers were significantly decreased significantly when compared with the baseline at 40 μM inositol ($*p<0.05$). When increasing the amount of inositol, the Oligo numbers rise and appear a statistical significance at level of 200 μM ($*p<0.05$). It demonstrated a consistent increase in the number of oligodendrocyte precursor cells and mature oligodendrocytes. Interestingly, the effect of inositol on Oligo number behaved differently from the condition containing PDGF in which the Oligo number decreased significantly ($**p<0.05$). It may relate to the different mechanisms by which the OPCs respond to higher level of inositol and to the PDGF. Taken together, it is a novel finding that inositol at higher level promotes OPCs differentiation into mature Oligo.

Example 4

Figure 4:
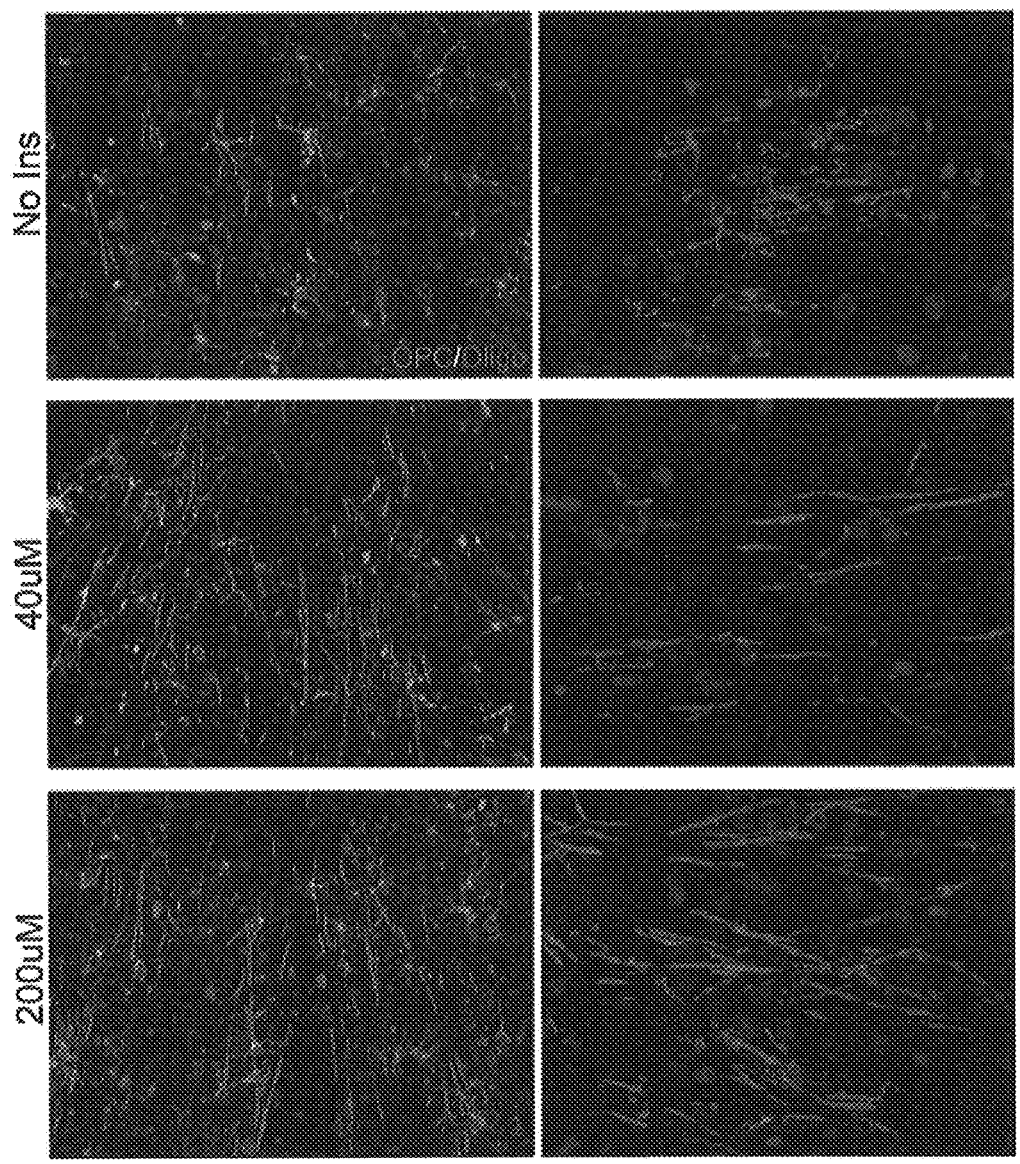
FIG. 4 shows the dual-fluorescence labeling of OPCs and oligodendrytes, as well as myelin deposition, resulting from the testing of Example 4.

FIG. 4 illustrates the utility of dual-fluorescence labeling of OPCs in green and oligodendrocytes (Oligo) in red (left), as well as myelin deposition along the DRG neuronal fibers in red (right). It is to examine a dose-response of the inositol on oligodendrocyte-DRG coculture. Inositol was added to purified oligodendrocyte-DRG cocultures and cells were analyzed for effects on proliferation, survival differentiation and myelination. In the absence of inositol, although myelin was deposited, the amount of red labeling and appearance of myelin were inappropriate, as myelin displaced as amassing, not properly wrapping around the fibers like an elongated red fluorescent stripe. At the baseline condition containing 40 μM inositol (middle panel), myelin was wrapping around the neuronal fiber displaced as stripes in red fluorescence. In the high level of inositol at 200 μM, it was demonstrated that more myelin has been deposited along the neuronal fibers. Taken together, it demonstrates that inositol at higher levels enhances myelin deposition.

Example 5

Figure 5:
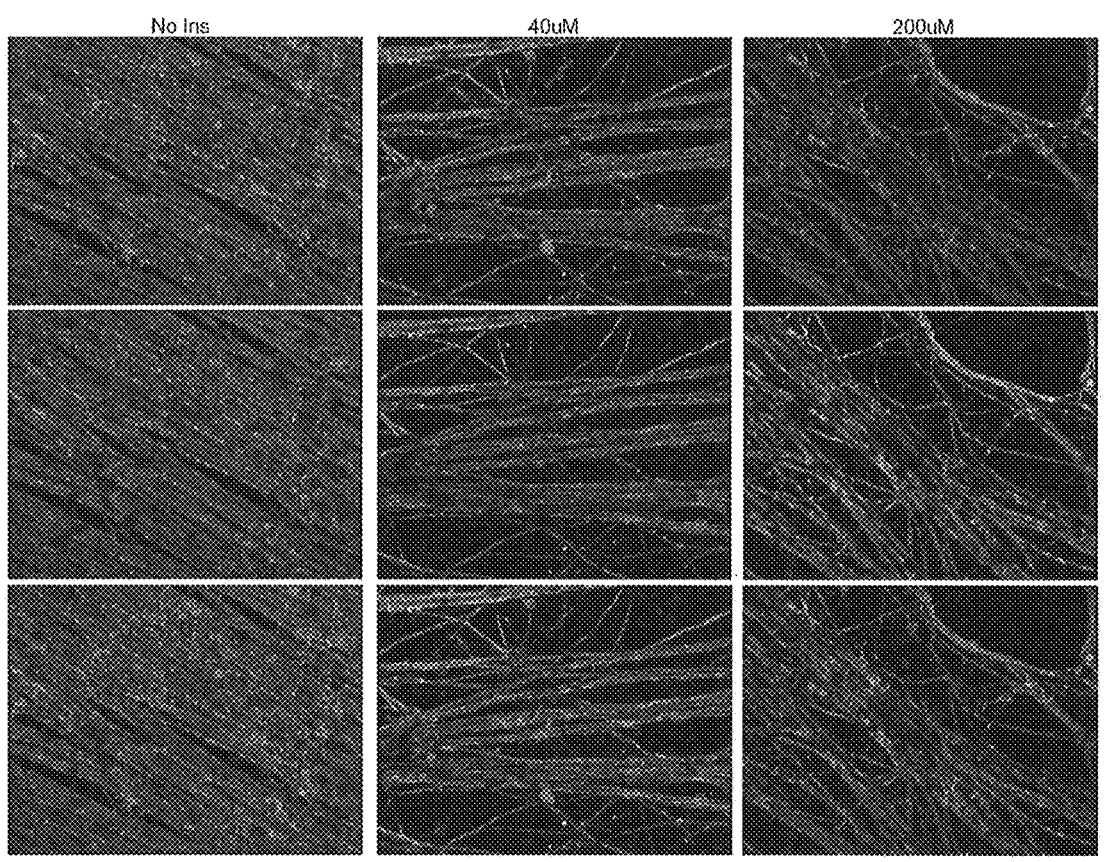
FIG. 5 illustrates a dose-response of inositol on myelin extent.

FIG. 5 illustrates the inositol effects on the control myelin extent in a dose-responsive manner. In the coculture system, neurofibers were included to validate the effects on myelin extent. In the absence of inositol, few myelin internodes were formed compared to the control base medium at 40 µM. Additionally, oligodendrocytes formed more and longer myelin internodes at 200 µM compared to the controls. Taken together, oligodendroglia rely on neuronal inositol for survival, proliferation, differentiation and the instruction of the generation of the appropriate number of myeline internodes and the extent of wrapping.

Example 6

Figure 6:
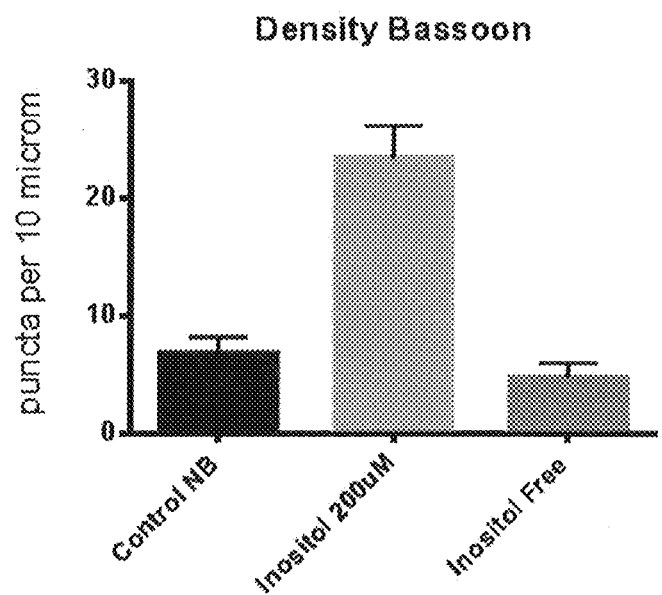
FIGS. 6 and 7 illustrate the Density Bassoon and Density Homer counts resulting from the testing of Example 6.
Figure 7:
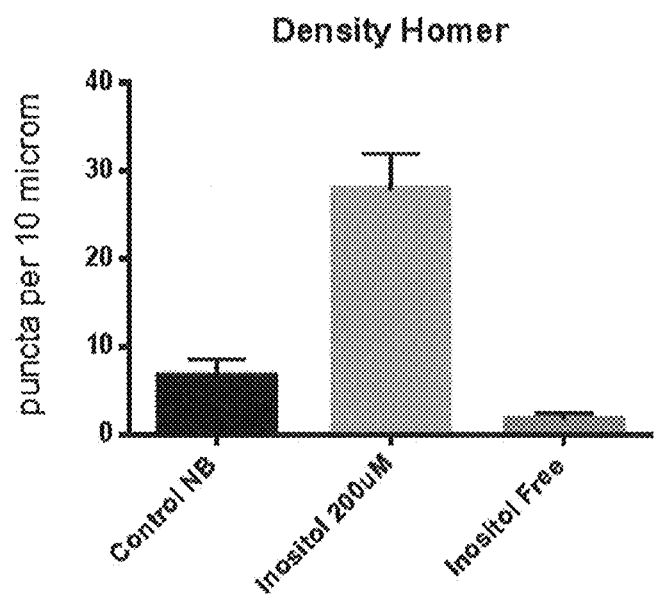

Primary hippocampal neurons were prepared from rats at E18. In brief, dissected hippocampi were incubated in 0.05% trypsin at 37° C. for 20 minutes and plated at a density of ~30,000 cells per coverslip. Dissociated cells were plated on poly-L-lysine and incubated in a cell culture incubator with 5.0% $CO_2$. Cytosine arabinoside was added at a final concentration of 2 µM per well 2 days in vitro to prevent glia cell overgrowth. For studies of inositol, neurons were either grown in inositol-free medium or in inositol-free medium supplemented with 40 µm inositol. After day 4 in vitro, neurons were grown either in inositol-free medium or in inositol-free medium supplemented with 40 µm or 200 µM inositol. At the first time of treatment at 4 days in vitro, the entire medium was exchanged for fresh medium containing nutrients, or control medium without nutrients. At the time of subsequent nutrient additions, approximately ½ of the medium was exchanged and replaced with nutrient-containing medium or control medium without nutrients. Neurons were processed for immunostaining at 14 days in vitro, i.e. after 10 days of chronic treatment. The data show that Increasing inositol from standard 40 µM to 200 µM substantially elevates the density of synaptic specializations. We determined this both by automated quantitative immunostaining for the presynaptic marker Bassoon or excitatory postsynaptic Homer, as shown in FIGS. 6 and 7 ($p<0.05$).

Figure 8:
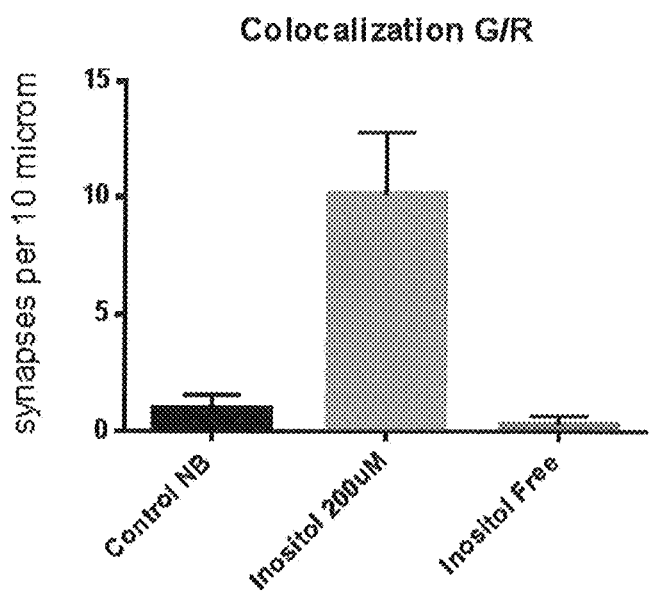
FIG. 8 illustrates the colocalization of synaptic sites resulting from the testing of Example 6.
Figure 9:
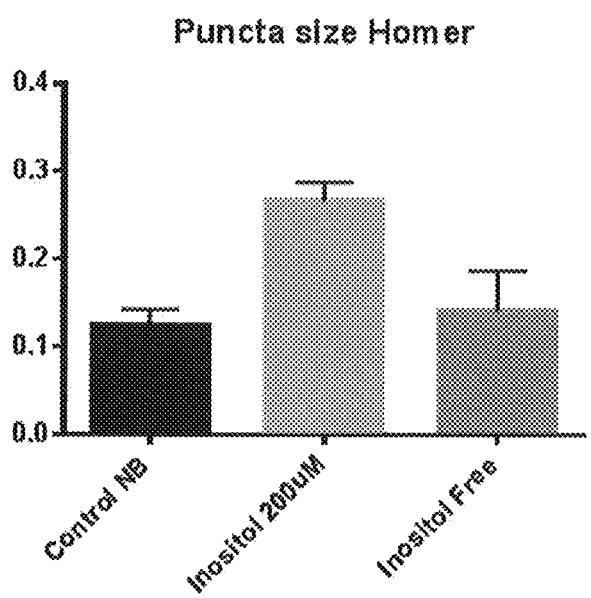
FIG. 9 illustrates the synaptic site sizes resulting from the testing of Example 6.

A strong inositol effect was also seen when the density of synaptic sites where both Bassoon and Homer co-localize was measured, as illustrated in FIG. 8, suggesting the functional synaptic development ($p<0.05$). Further, the experiment supports that the size of postsynaptic sites is larger when inositol is added, indicating more efficient synaptic transmission ($p<0.05$) (see, FIG. 9).

Figure 10:
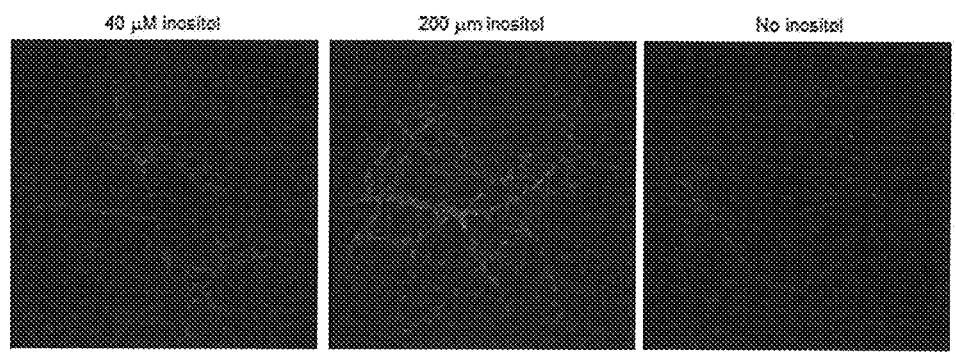
FIG. 10 shows the effects of inositol on synaptic development under the florescent microscopy resulting from the testing of Example 6.

Confocal imaging was performed on a Leica TCS SPE DM2500 microscope equipped with one spectral PMT. Fluorochromes imaged include Alexa 488, Alexa 555, and Alexa 647 (Invitrogen). Green fluorescence represents Bassoon presynaptic, red Homer postsynaptic, blue MAP2 dendrites. Depletion of inositol causes poor health of the neurons (right panel in FIG. 10). There was noticeable lack of growth and synapses which was visible while imaging. However, inositol significantly promotes the overall health of neurons at 40 and 200 µM, respectively. Elevated level of inositol supplement significantly enhances the formation of functional synapses and overall neuron health (Left panel, in FIG. 10).

Example 7

This example illustrates an embodiment of a nutritional composition according to the present disclosure.

| Nutrient | per 100 kcal |
| --- | --- |
| Protein (g) | 2 |
| Fat (g) | 5 |
| Carbohydrates (g) | 11 |
| Prebiotic (g) | 0.6 |
| Beta glucan (mg) | 9 |
| Polar lipids (mg) | 100 |
| Lactoferrin (mg) | 90 |
| Probiotic(s) (cfu) | $1 \times 10^8$ |
| DHA (mg) | 22 |
| ARA (mg) | 40 |
| Vitamin A (IU) | 400 |
| Vitamin D (IU) | 75 |
| Vitamin E (IU) | 2 |
| Vitamin K (mcg) | 12 |
| Thiamin (mcg) | 120 |
| Riboflavin (mcg) | 200 |
| Vitamin B6 (mcg) | 100 |
| Vitamin B12 (mcg) | 0.5 |
| Niacin (mcg) | 1100 |
| Folic acid (mcg) | 20 |
| Panthothenic acid (mcg) | 600 |
| Biotin (mcg) | 4 |
| Vitamin C (mg) | 18 |
| Choline (mg) | 30 |
| Calcium (mg) | 120 |
| Phosphorus (mg) | 60 |
| Sodium (mg) | 28 |
| Potassium (mg) | 140 |
| Chloride (mg) | 100 |
| Iodine (mcg) | 22 |
| Iron (mg) | 2 |
| Zinc (mg) | 1.2 |
| Manganese (mcg) | 25 |
| Copper (mcg) | 100 |
| Selenium (mcg) | 4 |
| Endogenous Inositol (mg) | 6 |
| Exogenous Inositol (mg) | 24 |
| Carnitine (mg) | 3 |
| Taurine (mg) | 8 |
| Adenosine monophosphate (mg) | 1 |
| Cytidine monophosphate (mg) | 4 |
| Guanosine monophosphate (mg) | 0.8 |
| Uridine monophosphate (mg) | 1 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A method for enhancing myelin deposition in a pediatric subject, the method comprising administering to the pediatric subject a nutritional composition comprising:

about 2 g/100 kcal to about 7 g/100 kcal of a fat or lipid;

about 1 g/100 kcal to no greater than about 7 g/100 kcal of a protein or protein equivalent;

about 5 g/100 kcal to about 25 g/100 kcal of a carbohydrate; and about 12 mg/100 kcal to about 40 mg/100 kcal of inositol, wherein the inositol comprises exogenous inositol and inherent inositol, wherein a ratio of the exogenous inositol to the inherent inositol is at least 75:25, and wherein administration of the nutritional composition to the pediatric subject enhances myelin deposition in the neurons of the pediatric subject.

2. The method of claim 1, wherein the nutritional composition further comprises at least one long chain polyunsaturated fatty acid.

3. The method of claim 2, wherein the at least one long chain polyunsaturated fatty acid includes at least one of docosahexaenoic acid or arachidonic acid.

4. The method of claim 3, wherein the at least one long chain polyunsaturated fatty acid is present from about 5 mg/100 kcal to about 75 mg/100 kcal.

5. The method of claim 1, wherein the nutritional composition further comprises docosahexaenoic acid, arachidonic acid, phosphatidylethanolamines, sphingomyelin, alpha-lipoic acid, epigallocatechin gallate, sulforaphane, or combinations thereof.

6. The method of claim 1, wherein the nutritional composition further comprises lactoferrin present at a level of about 10 mg/100 kcal to about 200 mg/100 kcal.

7. The method of claim 1, wherein the nutritional composition further comprises a prebiotic composition comprising polydextrose and galactooligosaccharides, wherein the prebiotic component comprises at least 20% w/w polydextrose and galactooligosaccharides and mixtures thereof.

8. The method of claim 1, wherein the nutritional composition is an infant formula or a growing up milk.

* * * * *